United States Patent
Bhatnagar et al.

(10) Patent No.: US 6,492,536 B2
(45) Date of Patent: Dec. 10, 2002

(54) STEROIDS, THEIR USE AS MEDICAMENTS, THEIR PREPARATION PROCESS, THE INTERMEDIATES OF THIS PROCESS AND THE COMPOSITIONS CONTAINING THEM

(75) Inventors: Neerja Bhatnagar, Savigny sur Orge (FR); Andre Claussner, Villemomble (FR); Christian Marchandeau, Annet sur Marne (FR); Michele Resche Rigon, Paris (FR); Jean-Georges Teutsch, Pantin (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/891,558

(22) Filed: Jun. 25, 2001

(65) Prior Publication Data
US 2002/0002155 A1 Jan. 3, 2002

Related U.S. Application Data

(62) Division of application No. 09/171,347, filed as application No. PCT/FR97/00693 on Apr. 17, 1997, now Pat. No. 6,274,572.

(30) Foreign Application Priority Data

Apr. 18, 1996 (FR) ............................................. 96 04845

(51) Int. Cl.⁷ ................................. C07J 3/00; C07J 1/00
(52) U.S. Cl. ....................... 552/646; 552/610; 552/633; 552/646; 552/647
(58) Field of Search ................................ 552/610, 633, 552/647, 646

(56) References Cited

U.S. PATENT DOCUMENTS

| | | | | |
|---|---|---|---|---|
| 2,837,544 A | * | 6/1958 | Fried | 260/397.45 |
| 3,232,839 A | * | 2/1966 | Keislich et al. | 167/77 |
| 5,223,493 A | * | 6/1993 | Boltralik | 514/167 |
| 5,420,120 A | * | 5/1995 | Boltralik | 514/172 |

* cited by examiner

Primary Examiner—Sabiha Qazi
(74) Attorney, Agent, or Firm—Bierman, Muserlian and Lucas

(57) ABSTRACT

The subject of the invention is the products of formula (I):

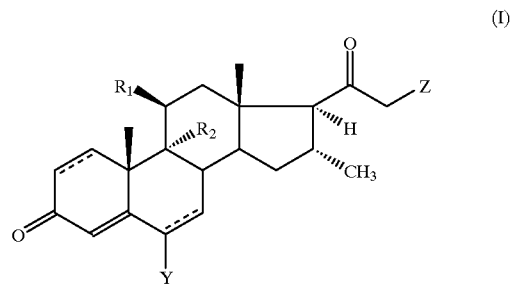

in which either $R_1$ represents halogen, hydroxyl, $(C_1-C_8)$ alkyloxy or $(C_1-C_{12})$ acyloxy, and $R_2$ represents halogen or hydrogen, or $R_1$ and $R_2$ form together a double bond, Z is chosen from optionally substituted $(C_1-C_8)$ alkylthio, optionally substituted arylthio, $(C_1-C_8)$ alkyloxy, halogen, cyano, mercapto, thiocyanato and $(CH_2)_{0-1}-CO_2H$, optionally esterified, Y represents hydrogen or methyl, the dotted line in position 1–2 or 5–6 optionally representing a second bond, as well as their addition salts, their preparation process, the intermediates of this process and the pharmaceutical compositions containing them.

1 Claim, No Drawings

STEROIDS, THEIR USE AS MEDICAMENTS, THEIR PREPARATION PROCESS, THE INTERMEDIATES OF THIS PROCESS AND THE COMPOSITIONS CONTAINING THEM

This application is a division of U.S. patent application Ser. No. 09/171,347 filed Oct. 16, 1998, now U.S. Pat. No. 6,274,572 which is a 371 of PCT/FR97/00693 filed Apr. 17, 1997.

The subject of the present invention is steroids, their use as medicaments, their preparation process and the intermediates of this process, and the pharmaceutical compositions containing them.

The subject of the invention is the products of general formula (I):

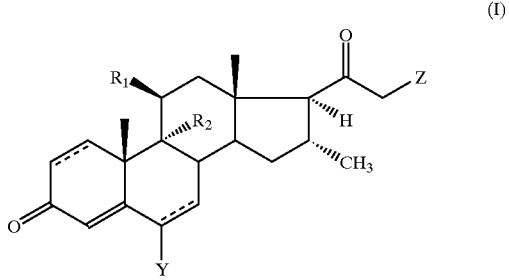

in which either $R_1$ represents a halogen atom, a hydroxyl radical, an alkyloxy radical containing 1 to 8 carbon atoms, an acyloxy radical containing 1 to 12 carbon atoms, and $R_2$ represents a halogen atom or a hydrogen atom, or $R_1$ and $R_2$ form together a second bond, Z is chosen from alkyloxy groups containing 1 to 8 carbon atoms, non-substituted or substituted alkylthio groups containing 1 to 8 carbon atoms, non-substituted or substituted arylthio groups containing 6 to 12 carbon atoms, halogen, cyano, mercapto, thiocyanato, $CO_2A$ and $CH_2CO_2A$ groups, A being a hydrogen atom or an alkyl group containing 1 to 8 carbon atoms, Y represents a hydrogen atom or a methyl, the dotted line in position 1–2 or 5–6 optionally representing a second bond, as well as their addition salts with acids or bases, it being understood that 9α-fluoro-11β-hydroxy-16α-6-methyl-21-chloro-pregna-1,4-diene-3,20-dione is excluded and it being understood that when $R_1$ and $R_2$ form together a double bond, Z is not a halogen atom.

By halogen atom is meant fluorine, bromine, chlorine and iodine atoms.

By alkyloxy and alkylthio radical containing 1 to 8 carbon atoms is preferably meant methoxy, ethoxy, propoxy, butyloxy radicals and the corresponding sulphurated radicals.

By acyloxy radical containing 1 to 12 carbon atoms is preferably meant acetyloxy, propionyloxy, butyryloxy and benzoyloxy radicals.

By alkyl radical containing 1 to 8 carbon atoms is meant the following radicals: methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl. It is quite particularly the methyl, ethyl, propyl, isopropyl, butyl, isobutyl and tert-butyl radicals.

By arylthio radical is preferably meant thiophenyl.

When Z is a substituted alkylthio or arylthio radical, it can be one of the following substituents: fluorine, chlorine, bromine, iodine, an alkyl radical such as methyl, ethyl, propyl, isopropyl, butyl, isobutyl, tert-butyl, an alkoxy radical such as methoxy, ethoxy, propyloxy, isopropyloxy, butyloxy, an alkylthio radical such as methylthio, ethylthio, propylthio, isopropylthio, butylthio, an amino radical, an alkylamino radical such as methylamino or ethylamino, a dialkylamino radical such as dimethylamino, diethylamino, methylethylamino, an optionally acylated hydroxyl radical, for example acetoxy, or a radical of formula: —O—CO—$(CH_2)_nCO_2H$ in which n=2 to 5, an acyl radical containing 2 to 8 carbon atoms such as acetyl, propionyl, butyryl, benzoyl, a free carboxy radical, an esterified carboxy radical such as alkoxy carbonyl, for example methoxy carbonyl or ethoxy carbonyl, a cyano radical, a trifluoromethyl radical, or a phenyl radical. The alkyl term contains 1 to 12 carbon atoms.

Of course, the expression "optionally substituted" indicates that one or more substituents, identical or different, can be present.

The substitution on the aryl can be carried out in ortho, meta or para position.

When Z is an optionally substituted alkylthio radical, the S—$CH_2$—$CH_2$-A' group is preferably meant in which A' is a hydroxyl, a halogen atom or an acetyloxy group.

When ring B is saturated, Y is preferably in α position.

The invention naturally extends to the salts of the compounds of formula (I), when these contain an amino function, with in particular the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonic such as methane and ethane sulphonic, arylsulphonic, such as benzene and paratoluene sulphonic and arylcarboxylic, and when the compounds of formula (I) contain an acid function, to the optionally substituted alkali metal, alkaline-earth and ammonium salts.

A more particular subject of the invention is the products of formula (I) as defined previously in which $R_1$ is a hydroxyl radical and $R_2$ is a fluorine atom, as well as their addition salts with acids or bases.

Among the compounds of the invention, there can preferably be mentioned the compounds of formula (I) for which ring B is saturated and Y is a hydrogen atom, as well as their addition salts with acids or bases.

A more particular subject of the invention is the products of formula (I) as defined previously in which Z is a cyano radical or an alkylthio group containing 1 to 8 carbon atoms.

Among the preferred products of the invention the following products can be mentioned:

9α-fluoro-11β-hydroxy-16α-methyl-pregn-4-ene-3,20-dioxo-21-carbonitrile methyl 3,20-dioxo-11β-hydroxy-16α-methyl-21-nor cholane 1,4-diene-24-oate 21-fluoro-11β-hydroxy-16α-methyl-pregna-1,4-diene-3,20-dione 21-thio-(2-hydroxyethylene)-9α,11β-dichloro-16α-methyl-pregna-1,4-diene-3,20-dione 21-thio-(2-acetyloxyethylene)-9α,11β-dichloro-16α-methyl-pregna-1,4-diene-3,20-dione 9α,11β-dichloro-21-fluoro-16α-methyl-pregna-1,4-diene-3,20-dione and quite particularly, 9α-fluoro-11β-hydroxy-16α-methyl-pregna-1,4-diene-3,20-dioxo-21-carbonitrile, 9α-fluoro-11β-hydroxy-16α-methyl-21-thiomethyl-pregna-1,4-diene-3,20-dione.

A subject of the invention is also a preparation process for the products of formula (I) characterized in that a product of general formula (II):

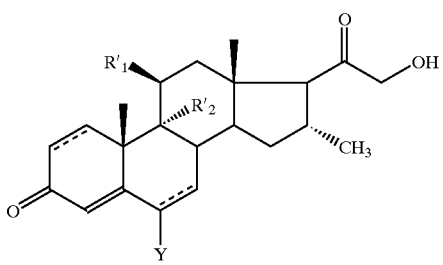

(II)

in which either R'₁ is a hydroxyl and R'₂ is a halogen or a hydrogen, or R'₁ is a halogen and R'₂ is a halogen or a hydrogen, or R'₁ and R'₂ form together a second bond and Y is as defined previously, is subjected to the action of an activation reagent of the alcohol of formula Hal-SO₂—B, Hal being a bromine or chlorine atom and B being an alkyl radical containing 1 to 6 carbon atoms, non-substituted or substituted by 1 to 5 halogen atoms, or a phenyl or naphthyl group non-substituted or substituted by 1 to 5 alkyl groups, containing 1 to 6 carbon atoms, in order to obtain a compound of general formula (III):

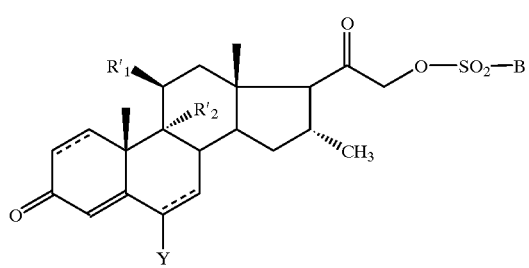

(III)

which product of formula (III) is subjected, if appropriate, to one or more of the following reactions in a suitable order, in order to obtain a product of general formula (I):

- action of a chlorination, iodination, bromination or fluorination reagent,
- action of an optionally substituted alkylthiol or arylthiol,
- action of a thioamide or of a thiourea followed by a hydrolysis,
- action of KCN,
- hydrolysis of the cyano group in acid medium then optionally esterification or salification
- successive action of CH₂(COOEt)₂, a saponification reaction then a decarboxylation reaction optionally followed by an esterification reaction,
- action of KSCN or NaSCN,
- action of an alcohol or an alcoholate,
- acylation reaction in position 11,
- alkylation reaction in position 11,
- reduction of the double bond in position 1-2,
- formation of the double bond in position 1-2,
- dehydration reaction in order to form a double bond in position 9-11,
- salification.

By B is preferably meant the —CH₃, —CF₃, —Ph—Me radicals.

The mesylate, tosylate or triflate of formula (III) are formed by the action, cold, of methane sulphonyl chloride, tosyl chloride or triflic anhydride on the corresponding alcohol of formula (II) in the presence of a base such as pyridine.

The formation of the 21-chlorinated derivative from the corresponding mesylate of formula (III) is carried out according to methods known to a man skilled in the art, in particular by the action of lithium or potassium chloride.

The formation of the 21-brominated derivative from the corresponding mesylate of formula (III) is carried out according to methods known to a man skilled in the art, in particular by the action of lithium or potassium bromide. The 21-brominated products can also be obtained directly from the corresponding alcohols by the action of hydrobromic acid or phosphorus tribromide.

The formation of the 21-iodinated derivative from the corresponding mesylate of formula (III) is carried out according to methods known to a man skilled in the art, in particular by the action of sodium or potassium iodide.

The formation of the 21-fluoro derivatives from the corresponding 21-chlorinated, 21-brominated or iodinated derivatives is carried out in particular by the action of potassium fluoride in glycol under reflux or by using crown ether, by phase transfer, or by ion-exchange resin. The formation of the 21-fluorinated derivative from the corresponding mesylate of formula (III) is carried out according to methods known to a man skilled in the art, in particular by the action of potassium fluoride.

The formation of the 21 alkylthio or arylthio derivatives from the corresponding 21-chlorinated derivative is preferably carried out by the action of an alkylthiol or arylthiol in the presence of a base such as triethylamine in tetrahydrofuran.

The formation of the corresponding thiol is preferably carried out by an indirect method such as the action of a thioamide or a thiourea followed by a hydrolysis.

The formation of the 21-cyano derivatives is carried out by the action of potassium cyanide in ethanolic medium on the corresponding 21-chlorinated, brominated or iodinated derivative.

The hydrolysis reaction of the 21-cyano groups is preferably carried out in the presence of hydrochloric acid or sulphuric acid.

The formation of the 21-thiocyanate derivatives is carried out by the action of potassium or sodium thiocyanate in ethanolic medium on the corresponding 21-chlorinated derivative.

The action of the ethyl malonate on the 21-chlorinated derivative in order to obtain the corresponding 21-CH(COOEt)₂ compound is preferably carried out in the presence of a strong base such as sodium hydride in an aprotic dipolar solvent such as HMPT.

The saponification reaction is carried out according to known methods, for example in the presence of soda in ethanolic medium.

The decarboxylation reaction is also carried out according to methods known to a man skilled in the art, in particular by thermal route.

The esterification reaction is carried out according to methods known to a man skilled in the art, in particular by the action of diazomethane. An acid chloride can also be formed beforehand then an aliphatic alcohol is reacted with it.

The formation of the 21-alkyloxy derivatives is preferably carried out by the action of an aliphatic alcohol such as CH₃OH or nBuOH on the 21-chlorinated derivative in an aprotic dipolar solvent such as dimethylsulphoxide in the presence of a base such as soda.

The salification reactions can be carried out under the usual conditions. The operation is carried out for example in the presence of ethanolic soda. A sodium salt can also be used such as sodium or potassium carbonate or acid carbonate.

The dehydration reaction of the compounds of general formula (I), (II) or (III) in which $R_1$ is a hydroxyl and $R_2$ is a hydrogen atom, in order to obtain the compounds of formula (I) with a double bond in position 9–11 is carried out according to the usual methods, amongst which there can be mentioned for example: the action of a mesylate chloride or triflic anhydride followed by a thermal reaction.

The products of formula (I) possessing a second bond in position 1-2 can be reduced to products of formula (I) saturated in position 1-2 by the action of a hydrogenation reaction according to the usual methods known to a man skilled in the art.

The formation of a double bond in position 1-2 can be carried out according to the usual methods by enzymatic or chemical route, in particular by the action of 2,3-dichloro-5,6-dicyanobenzoquinone (DDQ) in dioxane.

The acylation reaction of the hydroxyl in position 11 is carried out by the action of a carboxylic acid or a carboxylic anhydride.

The alkylation reaction of the hydroxyl in position 11 is carried out for example by the action of an alkyl iodide in the presence of a base such as potassium tertbutylate in a solvent such as tetrahydrofuran.

A subject of the invention is also, as new industrial products, the products of general formula (III), with the exception of the following compounds:

21-(methanesulphonyloxy)-16α-methylpregna-1,4,9(11)-trien-3,20-dione 21-(methanesulphonyloxy) 11β-hydroxy-16α-methyl-pregna-1,4-dien-3,20-dione 21-(4-methylphenylsulphonyloxy)-16α-methyl-pregna-1,4,9(11)-trien-3,20-dione.

The products of formula (II) used as starting products of the preparation process are known in a general manner. They are in particular desoxymethasone (U.S. Pat. No. 3,232,839), 9α,11β-dichloro 16α-methyl 21-hydroxy pregna 1,4-diene-3,20-dione (Application for Certificate of Addition N2381065), 16α-methyl 1,4-pregnadiene-11β,21-diol-3,20-dione (U.S. Pat. No. 3,354,186), 6α,16α-dimethyl 1,4-pregnadiene-11β,21-diol-3,20-dione (U.S. Pat. No. 3,232,839) or 6α-fluoro,16α-methyl 1,4-pregnadiene-11β,21-diol-3,20-dione (U.S. Pat. No. 3,232,839).

Among the anti-inflammatory and immuno-suppressive molecules currently available, the glucocorticoids constitute one of the most powerful therapeutic classes.

Their use is nevertheless limited due to their numerous side effects, amongst which there can be mentioned:

retarding effect on the hypothalamo-pituitary-adrenal axis (HPA)

intolerance to glucose, which can precipitate the appearance of diabetes muscular fusion retardation of healing atrophy of the skin osteoporosis increased susceptibility to infections neurological disorders hypercholesterolemia.

The effects of the glucocorticoids are mediated by nuclear receptors belonging to the family of steroid receptors. These receptors are a "ligand-inductible" transcription factor which can positively or negatively modulate the transcription of the target genes. (Evans, R. M., 1988 Science, 240, 889–895), (Green, S., Kumar, V., Theulaz, I., Wahli, W., and Chambon, P. 1988 EMBO J., 7, 3037–3044), (Beato, M. 1989. Cell, 56, 335–344), (Jonat, C., Rahmansdorf, H. J., Park, K. K., Cato, A. C., Gebel, S., Ponta, H., Herrlich, P., 1990 Cell, 62, 1189–1204), (Pfahl, M. 1993 Endocrine Reviews, 14, 651–658).

The use of the mutants of the glucocorticoid receptors has allowed it to be established that distinct regions of these receptors are involved in the functions of transactivation or transrepression, and therefore, that these two functions are theoretically separable (Heck, S., Kullmann, M., Gast, A., Ponta, H., Rahmansdorf, H. J., Herrlich, P., and Cato, A. C. B. 1994 EMBO J., 13, 4087–4095).

The obtaining of ligands of the glucocorticoid receptor acting in vivo as anti-inflammatories, and deprived of transactivation function, would allow better tolerated molecules to be developed.

The compounds of general formula (I) have useful pharmacological properties:

1) Glucocorticoid Activity

The Applicant has, in fact, revealed a new class of glucocorticoids. Different animal models (rats, mice) have allowed the very powerful anti-inflammatory properties of the products of the invention to be revealed. In particular they possess a remarkable glucocorticoid activity by local route. (cf test for ear oedema induced by croton oil in a mouse, in vivo activity equivalent to or greater than prednisolone or dexamethasone).

2) Dissociated Activity

Furthermore, the products of the invention act via the following action mechanism: in fact these molecules allow the transactivation and transrepression functions of the receptor to be separated. They have a so-called "dissociated" activity on the transcription of the target genes.

The molecules according to the invention have been tested in models of HELA cells transfected with the GRE-tk-CAT plasmid (transactivation), or with the pColl-CAT plasmid (transrepression). (Cf. TEST 1)

These molecules like DEXAMETHASONE are capable of inhibiting the transcription of the collagenase promoter; on the other hand, in contrast to DEXAMETHASONE, they do not or hardly activate the transcription of the GRE-tk promoter.

As the described products have anti-inflammatory and immunosuppressive activities of the same order as PREDNISOLONE, the therapeutic uses are still the uses traditionally described for medicaments made from PREDNISOLONE.

They can for example be used for the treatment of allergic, dermatological, digestive, endocrinic, hematological, infectious, neoplastic, nephrological, neurological, ophthalmological, respiratory or rhumatological affections or illnesses. They are particularly useful for organ transplants to prevent rejection of the transplants but also for the treatment of local inflammatory reactions such as for example, oedemas, dermatoses, pruritus, the various forms of eczema, sun erythemas, tendinitis or sprains. They are also quite particularly useful for the treatment of ophthalmic inflammatory disorders.

Their dissociated activity makes the compounds of the invention particularly useful in the treatment of the illnesses mentioned above while reducing certain side effects.

Therefore a subject of the invention is the products of formula (I) as well as their addition salts with pharmaceutically acceptable acids or bases, as medicaments.

A more particular subject of the invention is the products of formula (I), as well as their addition salts with pharmaceutically acceptable acids or bases, as medicaments having a glucocorticoid activity.

A quite particular subject of the invention is the products of formula (I), as well as their addition salts with pharmaceutically acceptable acids or bases, as medicaments having a dissociated glucocorticoid activity, this dissociation allowing the side effects to be reduced or to disappear.

Among the medicaments of the invention there can be mentioned more particularly:

9α-fluoro-11β-hydroxy-16α-methyl-pregna-1,4-diene-3,20-dioxo-21-carbonitrile,

9α-fluoro-11β-hydroxy-16α-methyl-3,20-dioxo-pregn-4-ene-21-carbonitrile,

9α-fluoro-11β-hydroxy-16α-methyl-21-thiomethyl-pregna-1,4-diene-3,20-dione, methyl 3,20-dioxo-11β-hydroxy-16α-methyl-21-nor cholane 1,4-diene-24-oate, 21-fluoro-11β-hydroxy-16α-methyl-pregna-1,4-diene-3,20-dione.

Among the medicaments of the invention there can be mentioned quite particularly:

9α-fluoro-11β-hydroxy-16α-methyl-pregna-1,4-diene-3,20-dione-21-carbonitrile,

9α-fluoro-11β-hydroxy-16α-methyl-21-thiomethyl-pregna-1,4-diene-3,20-dione.

The useful posology varies according to the affection to be treated and the administration route. It can vary for example from 1 to 1000 mg per day for an adult by oral route.

The invention extends to the pharmaceutical compositions containing as active ingredient, at least one of the medicaments as defined above.

The compounds of formula (I) are used by digestive, parenteral or local route, for example by percutaneous route. They can be prescribed in the form of plain or sugar-coated tablets, capsules, granules, suppositories, ovules, injectable preparations, ointments, creams, gels, microbeads, implants, patches, which are prepared according to the usual methods.

The active ingredient(s) can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, preservatives.

The useful dose varies, in particular, according to the patient to be treated and the affection in question. It can be comprised, for example, between 1 and 4 applications per day of an ointment containing 0.1% to 5% of product of Example 1.

A quite particular subject of the invention is the pharmaceutical compositions which can be administered by local route, containing as medicaments the following compounds as described above.

EXAMPLES

Compounds of Formula (I)

Preparation 1: 9α-fluoro-11β-hydroxy-16α-methyl-21-chloro-pregna-1,4-diene-3,20-dione (cf Mol. and Cell. Endocrinal (1981) 22 153-168)

After dissolution of 6 g of desoxymethasone in 24 ml of pyridine, 6 g of lithium chloride then 6 ml of methane sulphonic acid chloride are added while maintaining a temperature of less than 50° C. then agitation is carried out for 2 hours at ambient temperature. The reaction medium is poured into water, separation is carried out and the crude product is washed and dried and purified by chromatography on silica, eluting with a chloroform/ethyl acetate mixture 2/8 in order to obtain 1.86 g of expected pure product.

M.P.=185° C.

Infrared

C=O 1726 and 1707 cm$^{-1}$

Example 1

9α-fluoro-11β-hydroxy-16α-methyl-21-thiomethyl-pregna-1,4-diene-3,20-dione

After dissolution of 1.86 g of the product of Preparation 1 in 20 ml of tetrahydrofuran (THF) and 2 ml of triethylamine (TEA), methylthiol is bubbled through for one hour at 0° C. and agitation is carried out for 48 hours at ambient temperature. The reaction medium is poured into water, separation is carried out, the crude product is washed and dried and purified by recrystallization from a methylene chloride ($CH_2Cl_2$) and isopropyl ether mixture in order to obtain 1.477 g of expected pure product. M.P.=166° C.

Infrared ($CHCl_3$)

OH 3620 cm$^{-1}$+associated

C=O 1715 (shoulder), 1694, 1666 cm$^{-1}$

C=C 1627, 1611 cm$^{-1}$

Example 2

9α-fluoro-11β-hydroxy-16α-methyl-pregna-1,4-diene-3,20-dione-21-carbonitrile 3.9 g of the product of Preparation 1, 39 ml of ethanol, 1.080 g of potassium cyanide (90%) and 1.6 ml of water are mixed together under an inert atmosphere and under reflux for one hour 30 minutes. After cooling down in an ice bath and adjustment to a pH of 4 by the addition of acetic acid, the mineral salts are separated off and evaporation is carried out under reduced pressure until 4.7 g of crude product is obtained which is purified by chromatography on silica, eluting with an ethyl acetate/benzene mixture 4/6. 2.7 g of expected pure product is obtained. M.P.=250° C.

Infrared ($CHCl_3$)

OH 3615 cm$^{-1}$+associated

C=O 1723, 1664 cm$^{-1}$

Δ1-4 1627, 1608 cm$^{-1}$

C≡N 2260 cm$^{-1}$

Example 3

21-chloro-9α-fluoro-11β-hydroxy-16α-methyl-pregn-4-ene-3,20-dione

The operation is carried out in an equivalent manner to Preparation 1, but starting with 8 g of 16α-methyl-9α-fluoro-pregn-4-ene-11β,21-diol-3,20-dione (FR1315629). 4.95 g of expected pure product is obtained, after recrystallization from 2,2-dimethoxypropane. M.P.=196° C.

Infrared ($CHCl_3$)

OH 3616 cm$^{-1}$+associated

C=O 1725, 1706 cm$^{-1}$

Δ4 1663, 1624 cm$^{-1}$

Example 4

9α-fluoro-11β-hydroxy-16α-methyl-3,20-dioxo-pregn-4-ene-21-carbonitrile

The operation is carried out as in Example 2 but starting with 3.450 g of the product of Example 3. 2.36 g of the expected pure product is obtained. M.P.=224° C.

Infrared ($CHCl_3$)

OH 3610 cm$^{-1}$+associated

C=O 1722 cm$^{-1}$

Δ4 1667, 1625 cm$^{-1}$

C≡N 2260 cm$^{-1}$

Example 5

Methyl 3,20-dioxo-11β-hydroxy-16α-methyl-21-norcholane 1,4-diene-24-oate

Stage A: 21-chloro-16α-methyl-pregna-1,4,9(11)-triene-3-20-dione 8.8 ml of methane sulphonyl chloride is added at 10° C. to a mixture, under an inert atmosphere, of 15 g of methyl 16α-methyl-21-hydroxy-pregna-1,4,9(11)-triene-3-20-dione in 40 ml of methyl ethyl pyridine, and the whole is agitated at ambient temperature for 5 hours. It is poured into an ice+water mixture, acidified by the addition of hydrochloric acid, filtration is carried out, followed by washing and drying. 16.2 g of expected crude product is obtained which is purified by chromatography, eluting with a benzene/ethyl acetate mixture 8/2. 13.4 g of expected pure product is obtained.

M.P.=154° C.

Stage B: ethyl 3,20-dioxo-23-ethoxycarbonyl-16α-methyl-21-norchola-1,4,9(11)-triene 24-oate.

13.9 g of the chlorinated product obtained in the preceding stage in 80 ml of HMPT is added to a mixture, under an inert atmosphere, of 1.860 g of 50% sodium hydride in 50 ml of HMPT and 6 ml of ethyl malonate, and agitation is carried out at ambient temperature for 4 hours. The reaction medium is poured into water, extraction is carried out with ethyl acetate, followed by drying and evaporation under reduced pressure. 21.5 g of crude product is obtained which is purified by chromatography, eluting with a benzene/ethyl acetate mixture 9/1. 16.4 g of expected pure product is obtained.

Stage C: 23-carboxy-3,20-dioxo-16α-methyl-21-norchola-1,4,9(11)-triene 24-oic acid.

16.4 g of the diester prepared in the preceding stage, 200 ml of ethanol and 100 ml of 2N soda are mixed together and the mixture is agitated for 3 hours at ambient temperature. After evaporation of the ethanol under reduced pressure, dilution is carried out by the addition of an ice+water mixture (1 liter) and acidification is carried out with hydrochloric acid. After filtration, washing and drying, 14.6 g of the expected product is obtained. M.P.=170° C.

Stage D: 3,20-dioxo-16α-methyl-21-norchola-1,4,9(11)-triene 24-oic acid.

The mixture constituted by 14.6 g of the diacid obtained in the preceding stage in 250 ml of HMPT is heated for 4 minutes using a metal bath pre-heated to 180° C., then the mixture is poured into 1500 ml of an ice+water mixture. The monoacid which precipitates is filtered off, washed then dried. 11.9 g of the expected product is obtained.

M.P.=208° C.

Stage E: methyl 3,20-dioxo-16α-methyl-21-norchola-1,4,9(11)-triene 24-oate

A solution of 13 g/l of diazomethane in dichloromethane is added to a solution of 11.9 g of the monoacid formed in the preceding stage in 250 ml of dichloromethane, then evaporation is carried out under reduced pressure. 12.3 g of expected product is obtained. M.P.=98° C.

Stage F: methyl-α-bromo-3,20-dioxo-11β-hydroxy-16α-methyl-21-norchola-1,4-diene 24-oate 7.3 g of N-bromo succinimide then, at 0–10° C., 7.3 ml of perchloric acid and 35 ml of water, are added to a mixture, under an inert atmosphere, of 10.8 g of methyl ester in 150 ml of acetone. After mixing for 2 hours at 0–5° C., the reaction medium is poured into 500 ml of water, filtration is carried out and the precipitate is dried. 12.8 g of the expected product is obtained. M.P.=230° C.

Stage G: methyl 3,20-dioxo-11β-hydroxy-16α-methyl-21-norchola-1,4-diene 24-oate.

18 g of chromus acetate is added to a mixture, under an inert atmosphere, of 12.8 g of bromhydrine prepared in the preceding stage in 50 ml of dimethylsulphoxide (DMSO) and 6 ml of thiophenol, then agitation is carried out for one hour at ambient temperature. The reaction mixture is then poured into 1 liter of water, extraction is carried out with ethyl acetate, the organic phase is washed and dried then evaporated under reduced pressure to obtain 16 g of the expected crude product which is purified by chromatography, eluting with a benzene/ethyl acetate mixture 7/3 then by recrystallization from warm ethanol. In this way 3.4 g of expected pure product is obtained. M.P.=166° C.

Infrared (CHCl$_3$)
C=O 1735 cm$^{-1}$ (ester), 1709 cm$^{-1}$ (20-keto)
C=C 1609 cm$^{-1}$, 1626 cm$^{-1}$, 1664 cm$^{-1}$
OH 3615 cm$^{-1}$

Example 6

Example of Pharmaceutical Composition Containing A Compound of Formula (I)

Tablets were prepared with 50 mg of product of Example 1 as active ingredient.

Product of Example 1 . . . 50 mg

Excipient (talc, starch, magnesium stearate)

PHARMACOLOGICAL STUDY OF THE PRODUCTS OF THE INVENTION

I) Study of the regulation of transcription in transfected Hela cells.

Hela cells (ATCC ref: CCL-2) are distributed in a 6-well plate, in a nutritive medium with a density of 4×10$^5$ cells/ml, 24 hours before the transfection, and are incubated at 37° C. The transitory transfections are produced according to the precipitate method with calcium phosphate. In the case of the study of transactivation, the cells are transfected with 1 μg of GRE-tk-CAT plasmid, 1 μg of polyII β-GAL plasmid and KS plasmid (Stratagene), s.q.f. 5 μg. In the case of the study of transrepression, the cells are transfected with 3 μg of ColI (−517/+63) CAT plasmid, 250 ng of pSV-cjun plasmid, 1 μg of polyII β-GAL plasmid and KS plasmid (Stratagene), s.q.f. 5 μg. The precipitate is left in contact with the cells for 16 hours. These are then rinsed and covered with the nutritive medium containing different concentrations of Dexamethasone or the products to be studied (10$^{-9}$M, 10$^{-8}$M, 10$^{-7}$M, 10$^{-6}$M). 24 hours after the addition of the products, the cells are lysed in 250 μl of MOPS-NaCl-Triton X-100 buffer. The CAT is dosed in the cellular extracts using the ELISA Kit (Boehringer Mannheim).

The standard glucocorticoids such as Dexamethasone cause an activation of the transcription of the GRE-tk promoter, and an inhibition of the transcription of the collagenase promoter.

|  | Concentration (M) | Activation of GRE-tk (%) | Inhibition of the ColI promoter (%) |
|---|---|---|---|
| Dexamethasone | 10$^{-9}$ | 7.34 +/− 2.57 | 42.16 +/− 5.46 |
|  | 10$^{-8}$ | 53.38 +/− 2.65 | 87.60 +/− 2.94 |
|  | 10$^{-7}$ | 89.48 +/− 2.26 | 96.63 +/− 1.78 |
|  | 10$^{-6}$ | 98.82 +/− 1.18 | 93.08 +/− 2.87 |

-continued

|  | Concentration (M) | Activation of GRE-tk (%) | Inhibition of the ColI promoter (%) |
|---|---|---|---|
| (Example 1) | $10^{-9}$ | 3.78 +/- 0.87 | 3.57 +/- 3.09 |
|  | $10^{-8}$ | 27.74 +/- 1.05 | 37.12 +/- 6.7 |
|  | $10^{-7}$ | 35.21 +/- 2.24 | 57.61 +/- 2.46 |
|  | $10^{-6}$ | 37.56 +/- 1.9 | 81.79 +/- 2.98 |
| (Example 2) | $10^{-9}$ | 0 | 20.61 +/- 3.19 |
|  | $10^{-8}$ | 1.34 +/- 1.33 | 36.2 +/- 1.39 |
|  | $10^{-7}$ | 10.45 +/- 4.33 | 81.32 +/- 1.82 |
|  | $10^{-6}$ | 16.92 +/- 3.55 | 75.57 +/- 1.34 |

2) Anti-Inflammatory Activity

Granuloma Test—Thymolytic Activity

The anti-inflammatory activity was studied according to the standard granuloma test. The technique used is a modification of the method of Meier and Coll. (Experentia, 1950, 6, 469). Female Wistar rats, weighing 90 to 100 g, receive an implantation of two cotton pellets of 10 mg each under the skin of the thorax. The products are immediately administered by oral route, a the rate of once a day for four days. The animals are then sacrificed. The pellets surrounded by the granuloma tissue formed, are weighed in the fresh state, then after eighteen hours at 60° C. The weight of the granuloma is obtained by deduction of the initial weight of the cotton.

The thymuses are also removed and weighed in order to determine the thymolytic activity of the products.

| Product of Example | Granuloma ED 50 (mg/kg/po) | Thymolysis ED 50 (mg/kg/po) |
|---|---|---|
| Dexamethasone | 0.1 | <0.05 |
| Prednisolone | 2.5 | 1.6 |
| EXAMPLE 1 | 5 | 2.5 |
| EXAMPLE 2 | >7 | 2.5 |

Ear Oedema Test Induced by Croton Oil

The products have also been tested in the model of the ear oedema of mice using croton oil according to the method described in Tonelli et al. (Endocrinology, 1965, 77, 625–634). An ear oedema is induced in male mice weighing 18 to 22 g, by using croton oil (2% v/v) in a pyridine-water-ether solution 4:1:14.6 (by volume). The animals are sacrificed 6 hours later, the ears are removed and weighed. The difference in weight between the ear treated with croton oil and the contralateral ear (non-treated) allows 100% of the oedema to be determined. The products to be tested are dissolved in the solution of croton oil and applied to the ear.

| Product of Example | Oedema using croton oil (mouse) ED 50 (μg/ear) |
|---|---|
| Dexamethasone | 1 |
| Prednisolone | 4 |
| EXAMPLE 1 | 10 |
| EXAMPLE 2 | 2 |

3) Immunosuppressive Activity.

The immunosuppressive activity was studied according to the retarded hypersensitivity test described in the article by Hambleton et al. (Agents and Actions, 990, 29, 328). Male Wistar rats weighing 150 to 160 g are sensitized on day 0 with a suspension of Mycobacterium Tuberculosis 4 mg/ml in parrafin oil by a sub-cutaneous injection at the base of the tail (0.1 ml/animal).

The products are administered by oral route from day 4 to 7.

On day 7, one hour after the last administration, the animals receive an injection of the soluble fraction of the antigen triggering the hypersensitivity reaction: 0.4 mg/rat in 0.2 ml by intraplantar route in a rear paw, the other receives the same quantity of solvent.

The oedema is measured 24 hours afterwards using an UGO BASIL plethysmometer from APELEX.

The activity of the products is evaluated by the percentage reduction in the increase of the injected paw relative to that of the control animals.

| Product of Example | Retarded hypersensitivity (M. Tuberculosis, rat) ED 50 (mg/kg) |
|---|---|
| Dexamethasone | 0.05 |
| Prednisolone | 5–20 |
| EXAMPLE 1 | 2.3 |
| EXAMPLE 2 | 1.5 |

What is claimed is:

1. A compound of the formula

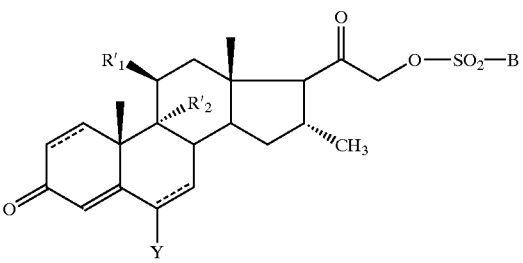

III where $R'_1$ is —OH and $R'_2$ is halogen or hydrogen or $R'_1$ is halogen and $R'_2$ is halogen or hydrogen or $R'_1$ and $R'_2$ together form a second bond, B is selected from the group consisting of a) alkyl of 1 to 5 carbon atoms unsubstituted or substituted with up to 5 halogens and b) phenyl and naphthyl unsubstituted or substituted with up to 5 alkyl of 1 to 6 carbon atoms, Y is hydrogen or methyl and the dotted line may be a second bond excluding 21-(methanesulfonyloxy)-16α-methyl-$\Delta^{1,4,9(11)}$-pregnatriene-3,20-dione, 21-(methanesulfonyloxy)-16α-$\Delta^{1,4}$-pregnadiene-11β-ol-3,20-dione and 21-(4-methyl-phenyl-sulfonyloxy)-16α-methyl-$\Delta^{1,4,9(11)}$-pregnatriene-3,20-dione.

* * * * *